United States Patent [19]

Fitzhugh

[11] Patent Number: 5,153,309
[45] Date of Patent: Oct. 6, 1992

[54] PROCESS OF MAKING TETRAHYDROPTEROYLPOLY-L-GLUTAMIC ACID DERIVATIVES

[75] Inventor: Anthony L. Fitzhugh, Frederick, Md.

[73] Assignee: The United States of America as represented by the Department of Health and Human Services, Washington, D.C.

[21] Appl. No.: 558,535

[22] Filed: Jul. 27, 1990

[51] Int. Cl.$^5$ .................. A61K 37/02; C07K 5/00
[52] U.S. Cl. .................. 530/333; 530/331; 530/332
[58] Field of Search .................. 530/331, 332, 333

[56] References Cited

PUBLICATIONS

Pawelczak et al. J. Med. Chem. vol. 32 No. 1 (Jan. 1989) 160–165.
Rosowsky & Yu Chem. Biol. Pteridines Rev. Biochem. vol. 4, 6th (1979) 273–277.
Rosowsky et al. J. Med. Chem. vol. 27 No. 5 (1984).
Krumdieck, C. L. & Baugh, C. M., Methods Enzymol.; vol. 66, 1980, 523–529.
D'Ari, L. & Rabinowitz, J. C., Methods Enzymol.; vol. 113, 1985, 169–183.
Nefkens, "Synthesis of alpha–Esters of N–Substituted Glutamic Acid", pp. 39–40.
Huennekens et al, Methods in Enzymology, vol. VI, Peptide Proc. Eur. symp. 5th (1963) pp. 802–815 (1963).
McGuire et al, The Journal of Biological Chemistry, vol. 255, No. 12, pp. 5776–5785 (Jun. 25, 1980).
Rees et al, Tetrahedron, vol. 42, No. 1, pp. 117–136 (1986).
Pohland et al, J. Am. Chem. Soc., vol. 73, No. 7, pp. 3247–3252 (Jul. 1951).

*Primary Examiner*—Merrell C. Cashion, Jr.
*Assistant Examiner*—B. Celsa
*Attorney, Agent, or Firm*—Birch, Stewart, Kolasch & Birch

[57] ABSTRACT

The invention is a method of synthesizing tetrahydropteroylpoly-L-glutamic acid derivatives starting from the mono-L-glutamic acid derivatives. The method has the advantage of not requiring any enzymes.

10 Claims, No Drawings

PROCESS OF MAKING TETRAHYDROPTEROYLPOLY-L-GLUTAMIC ACID DERIVATIVES

FIELD OF THE INVENTION

The invention is a method of synthesizing a tetrahydropteroylpoly-L-glutamic acid derivative starting from the tetrahydropteroyl-mono-L-glutamic acid derivative.

BACKGROUND

Folinic acid (also known as Leucovorin or Citrovorum factor) is an N-substituted derivative of L-glutamic acid bearing the chemical designation, N-[4[2-amino-5-formyl-1,4,5,6,7,8-hexahydro-4-oxo-6-pteridinyl)methyl]amino]benzoyl]-L-glutamic acid or 5-formyl tetrahydrofolic acid. Folinic acid has two chiral centers; one at the α-position of its glutamic acid group, and, the other at the C-6 carbon atom of its tetrahydropteroyl ring. Folinic acid differs in configuration at only one of these chiral centers because the glutamic acid group is derived exclusively from the L-form of this substituent. When prepared chemically using a reducing agent such as diethylamine borane [Forsch, R. A., Rosowsky, A., J. Org. Chem. 50, 2582-2583 (1985)], folinic acid consists of a 1:1 mixture of 6R and 6S forms. However, when isolated from biological sources folinic acid occurs only in the (6S)-form and, generally, contains 1 to 15 additional γ-linked L-glutamic acid residues.

A number of reports [Kalman, T. I., Chem. Biol. Pteridines, Int. Symp. Pteridines Folic Acid Deriv.: Chem., Biol. Clin. Aspects, 8th, 1986, 763-766, Edited by Cooper, B. A., Whitehead, V. M., de Gruyter, Berlin, Fed. Rep. Ger.; Schirch, V. et al., ibid, 887-898; Mackenzie, R. E., Baugh, C. M., Adv. Exp. Med. Biol., 163: Folyl and Anti-Folyl Polyglutamates, 1983, 19-34, Edited by Goldman, I. D., Chabner, B. A., Bertino, J. R., Plenum Press, New York, U.S.A.; Baggott, J. E., Krumdieck, C. L., Chem. Biol. Pteridines: Dev. Biochem., 4, 6th, 1978 (Pub. 1979), 347-351, Edited by Kisliuk, R. L., Brown, G. M., Elsevier/North-Holland, New York, U.S.A.] indicate that tetrahydropteroylpoly-L-glutamic acid derivatives have greatly enhanced substrate and/or inhibitor activity when assayed against several folic acid enzymes compared with the mono-L-glutamic acid forms. The availability of these derivatives has been limited by the difficulty encountered in producing large quantities of the (6S)-form of tetrahydrofolic acid [Rees, L. et al., Tetrahedron, 42, 117-136 (1986)]. Until now no direct purely chemical method existed for converting tetrahydropteroylmono-L-glutamic acid derivatives to their poly-L-glutamic acid forms.

SUMMARY OF THE INVENTION

An objective of this invention was to design a simple procedure for the production of pure (6R) and (6S)-tetrahydropteroylpoly-L-glutamic acid derivatives or mixtures thereof starting from the (6R) and (6S)-tetrahydropteroylmono-L-glutamic acid derivatives. A second objective of this invention was chemical intermediates produced by and used in the procedure.

DETAILED DESCRIPTION OF THE INVENTION

The compounds that can be made by the method of the invention have the formulas (IA) and (IB)

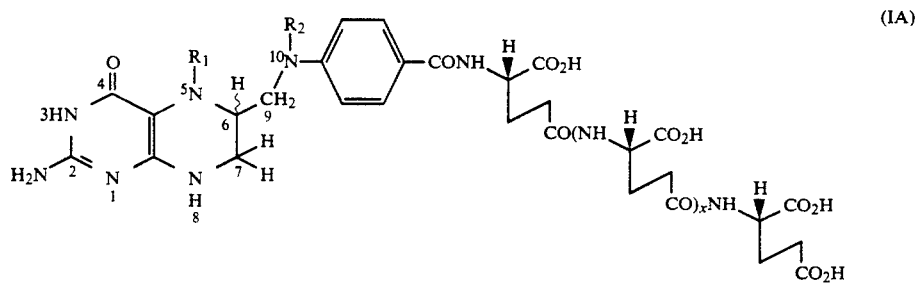

(IA)

wherein x is 0 to 14, $R_1$ and $R_2$ are independently H, $C_1$-$C_6$ alkyl, $C_1$-$C_6$ alkylcarbonyl, $C_1$-$C_6$ alkoxycarbonyl, $C_6$-$C_{10}$ arylcarbonyl, $C_6$-$C_{10}$ aryloxycarbonyl, or —CHO, each of which (except the —CHO) may be substituted by halogen, $C_1$-$C_6$ alkoxy or phenyl; e.g. acetyl, t-butyl, 2,2-dichloroacetyl, benzoyl, t-butoxy carbonyl, benzyloxy carbonyl; or $R_1$ and $R_2$ together form a one carbon bridge between the nitrogen atoms at positions 5 and 10. The chiral carbon atom at position 6 can take the R or the S configuration or mixtures of the R and S configurations (especially equal molar mixtures). The structure shown in formula (IA) shows the poly-L-glutamic acid moiety being completely γ-linked, i.e., each glutamic acid moiety is linked to the next one through its γ-carboxylic acid moiety rather than the α-acid. However, the method of the invention includes the synthesis of tetrahydropteroylpoly-L-glutamic acid derivatives wherein the poly-L-glutamic acid moiety also includes some α-linked glutamic acid moieties. The α-linked glutamic acid moieties could be anywhere in the poly-L-glutamic acid except the amino end. Such compounds exist in nature (Ferone, et al., J. Biol. Chem., 261 16356-16362, 1986: and Ferone, et al., J. Biol. Chem., 261, 16363-16371, 1986, both of which are hereby incorporated by reference). Most particularly the tetrahydropteroylpoly-L-glutamic acid derivatives with α-linked glutamic acids have the structure of formula (IB)

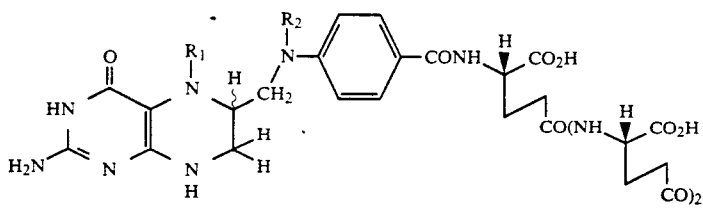

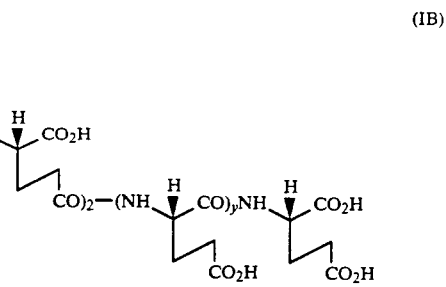

(IB)

wherein y is 2-15, more particularly 2-6 and most preferably 4, $R_1$ and $R_2$ are defined the same as for the compound of formula (IA). The more preferred compounds of formulae (IA) and (IB) have the (6S) configuration.

Three reports guided the development of this invention: i) the observation that in the presence of one equivalent of base, the α-carboxyl group of an N-substituted L-glutamic acid derivative ionizes approximately 70 to 100 times more than the γ-carboxyl group; hence, reaction with an alkyl or aryl halide should result in the preferential formation of an α-monoester of folinic acid [Nefkens, G. H. L., Peptides, Proc. European Symp., 5th, 1962 (Pub. 1963), 39–40, Oxford; Nefkens, G. H. L., Nivard, R. J. F., Rec. Trav. Chem., 83, 199–207 (1964), which are both incorporated by reference]; ii) the ease with which α, γ-diesters of folinic acid are formed with alkyl/aryl halides, and excess base in DMSO [Rosowsky, A., Yu, C-S., Chem. Biol. Pteridine: Dev. Biochem., 4, 6th, 1978 (Pub. 1979), 273–277, Edited by Kisliuk, R. L., Brown, G. M., Elsevier/North-Holland, New York, U.S.A., which is hereby incorporated by reference in its entirety]; iii) the development of a large scale fractional crystallization method for the resolution of the (6R) and (6S)-forms of folinic acid, calcium salt [Mueller, H. R. et al., Int. Pat. PCT Int. Appl. WO 88/08,844 (Cl. C07D475/04), 15 May 1987, which is incorporated by reference in its entirety].

It has been found in this invention that tetrahydropteroylpoly-L-glutamic acid derivatives can be prepared following conversion to their α-monoester form and subsequent γ-coupling with mono- or poly-L-glutamyl substituents. The invention provides a process for the preparation of pure (6R) or (6S)-tetrahydropteroylpoly-L-glutamic acid derivatives or mixtures thereof. The invention comprises the steps of: 1) attachment of an alkyl, aryl or trialkylsilyl substituent preferentially on the α-carboxyl group of a tetrahydropteroylmono-L-glutamic acid derivative to produce an α-monoesterified protected derivative; 2) direct coupling of the tetrahydropteroyl α-monoester with either mono- or poly-L-glutamic acid (in suitably protected form) or salt or ester to the γ-carboxyl group using standard methods of making peptide bonds [see The Peptides: Major Methods of Peptide Bond Formation, 1979, 1, 1–495, Edited by Gross, E., Meienhofer, J., Academic Press, New York, U.S.A., which is incorporated by reference]; and, 3) deprotection to give the desired tetrahydropteroylpoly-L-glutamic acid derivative or salt thereof. The advantage of the process over the prior art is that it is a wholly chemical process, with no enzymatic step. The prior art method entails (see D'Ari et al., Methods of Enzymology, Vol. 113, pages 169–182, 1985, which is incorporated by reference) using a folylpoly-L-glutamate derivative which must undergo enzyme-mediated reduction in order to form the desired (6S)-tetrahydropteroylpoly-L-glutamate. At this stage of the art this requires,: (i) purification of the enzyme, dihydrofolate reductase, from a biological source; (ii) a reducing cofactor, nicotinamide adenine dinucleotide phosphate reduced form (NADPH), to act as a hydrogen donor; and, (iii) in the case of a large scale (grams) preparations, an enzymatic method (e.g., isocitrate dehydrogenase, glucose-6-phosphate dehydrogenase/creatine kinase etc.) for recycling the oxidized cofactor, nicotinamide adenine dinucleotide phosphate, (NADP+, see Whitesides, G. M., Wong, C. H., Aldrichimica Acta, 16, 27–34, 1983; Whitesides, G. M. Wong, C-H Angew. Chemie, (Int. Ed.) 24, 617–718, 1985). The use of enzymes and cofactors is expensive and limits the quantity of product that can be made.

The steps in the synthesis are now written out in more detail and in structural terms:

STEP 1

Synthesis of the α-Monoesterified Intermediate A compound of the formula (II)

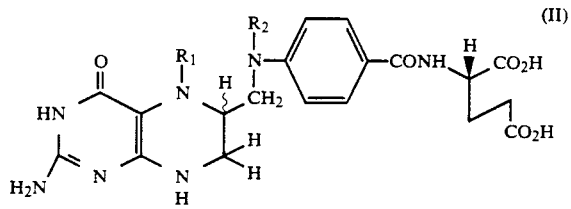

(II)

wherein $R_1$ and $R_2$ are the same as in formula (I) above, is esterified at the α-carboxyl position to form the α-monoesterified intermediate compound of formula (III)

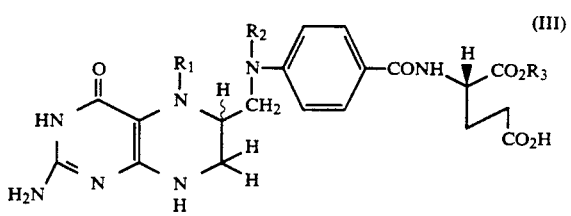

(III)

$R_3$ is any aliphatic or aromatic moiety which protects the α-carboxylic acid group in STEP 2, and which is easily removed at the end of the reaction under conditions which do not adversely effect the rest of the molecule. More specifically, $R_3$ can be $C_1$–$C_8$ alkyl, substituted $C_1$–$C_8$ alkyl, $C_5$–$C_6$ cycloalkyl, substituted $C_5$–$C_6$ cycloalkyl, $C_6$–$C_{10}$ aryl (phenyl and naphthyl), substituted $C_6$–$C_{10}$ aryl, $C_6$–$C_{10}$ aryl $C_1$–$C_8$ alkyl, substituted $C_6$–$C_{10}$ aryl $C_1$–$C_8$ alkyl, diphenylmethyl, substituted diphenylmethyl and tri-$C_1$–$C_4$ alkylsilyl. The substituents can be any organic or inorganic moiety which do not adversely effect the $R_3$ group's ability to function as an easily removable protecting group. Examples of the substituents, which can number up to three, are methyl, ethyl, $C_1$–$C_3$ alkoxy, $C_1$–$C_3$ thiol and halogen. By halogen is meant fluorine, chlorine, bromine and iodine, preferably chlorine and bromine. By alkyl is meant a straight chain saturated hydrocarbon moiety.

Preferably $R_3$ is $C_1$–$C_6$ alkyl, substituted $C_1$–$C_6$ alkyl, $C_5$–$C_6$ cycloalkyl, phenyl, substituted phenyl, benzyl, substituted benzyl, diphenylmethyl and triethylsilyl.

Most preferably $R_3$ is methyl, ethyl, propyl, butyl, sec-butyl, t-butyl, pentyl, hexyl, cyclopentyl, cyclohexyl, methoxymethyl, ethoxymethyl, methylthiomethyl, 2,2,2-trichloroethyl, 2-bromoethyl, phenyl, benzyl, 2-chlorobenzyl, 2,6-dichlorobenzyl, diphenylmethyl and triethylsilyl.

The esterification reaction can be carried out by any means known to the art, (see, for example Nefkens et al., Rec. Trav. Chem., 83, 199–207, 1964, which is incorporated by reference). Most preferably the reaction is carried out by reacting a compound of the formula $R_3$-X, wherein $R_3$ is the same as described above, and X is halogen, preferably bromine, with the compound of formula (II). The reaction is carried out in the presence of base in a polar aprotic solvent. Suitable bases are carbonates, bicarbonates, hydroxides, hydrides, amides and amines (both aliphatic and aromatic). The base should be strong enough to quantitatively remove the α-carboxyl hydrogen. Examples of suitable bases include $NaHCO_3$, $Na_2CO_3$, $NaH$, $NaNH_2$, $KHCO_3$, $K_2CO_3$, $LiHCO_3$, $Li_2CO_3$, $NaOH$, $KOH$, $LiOH$, triethylamine, diisopropylethylamine, 4-methylmorpholine, 2,6-di-t-butylpyridine, tetrabutylammonium hydroxide and the like. The molar ratio of base to the compound of formula (II) should be in the ratio of 1.5 to 0.5, preferably about 1.0. Suitable polar aprotic solvents are DMA (dimethylacetamide), DMF (dimethylformamide), DMSO (dimethylsulfoxide) and HMPT (hexamethylphosphoramide). The molar ratio of $R_3$-X to compound (II) is in the range of 1.5 to 0.5 and preferably is about 1. The temperature range for the reaction with $R_3$-X is from about $-50°$ C. to about $+150°$ C., preferably about $+25°$ C. The reaction is preferably carried out at atmospheric pressure. The esterification reaction results in mostly the desired α-monoesterified product, however, a small (about 10%) of the product formed is the γ-monoesterified product. The α-monoesterified product is purified by high pressure liquid chromatography, column chromatography or fractional crystallization.

STEP 2

Coupling Reaction

The compound of formula (III) produced in Step 1 is coupled to compounds of formulae (IVA) or (IVB):

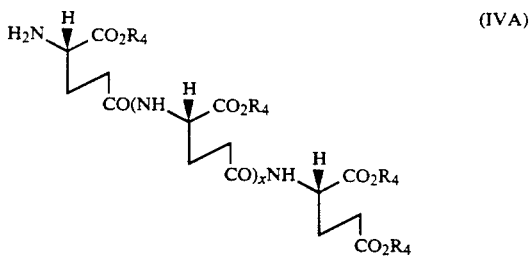

wherein x is 0 to 14, and $R_4$ is a carboxyl protecting group which can be chosen from the same moieties as $R_3$ above. Preferably $R_4$ is methyl, ethyl, propyl, butyl, sec-butyl, t-butyl, pentyl or hexyl; and most preferably $R_4$ is ethyl or t-butyl.

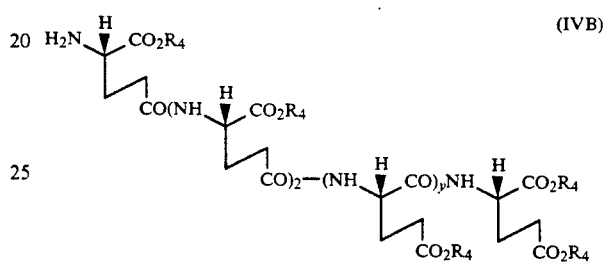

wherein y is 1–15, preferably 1–6 and most preferably 3; and $R_4$ is the same as defined above. The coupling reaction produces compounds of formulae (VA) or (VB):

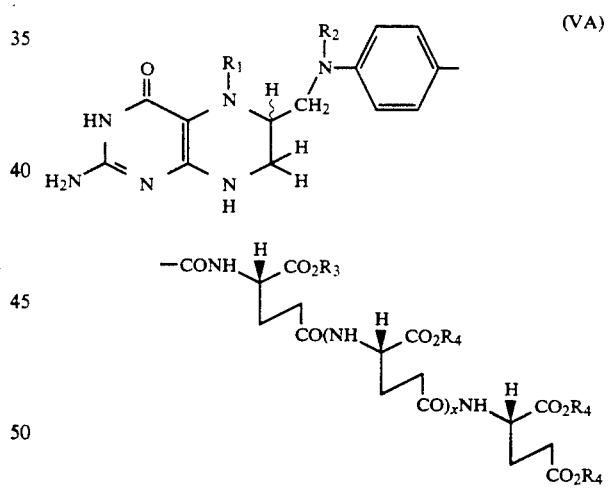

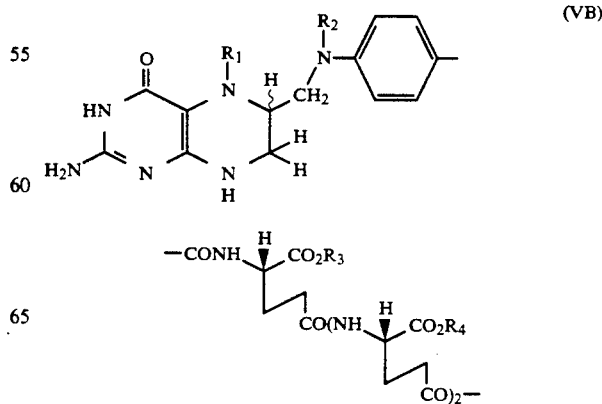

-continued

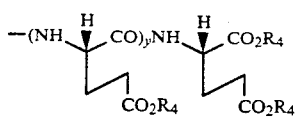

wherein $R_1$, $R_2$, $R_3$, $R_4$, x and y are defined as above. The coupling reaction can be any of the standard methods known in the art of peptide synthesis, see Gross et al., supra, particularly pages 106-309. Examples include the activation of the carboxyl group with reagents such as DCC (N', N'-dicyclohexylcarbodiimide), EEDQ (N-ethoxycarbonyl-2-ethoxy-1,2-dihydroquinoline), 1', 1'-carbonyldiimidazole, diphenylchlorophosphate and the like. Compounds of formulae (IVA) and IVB) are commercially available; also, the L'Ari et al., reference (supra) teaches how to make these compounds. Methods of making the protected species of formulae (IVA) and (IVB) are also taught by Krumdieck, et al., *Biochem.*, 8, 1568-1572, 1969; Meienhofer, J., et al., *J. Org. Chem.*, 35, 4137-4140, 1970; Drey, C. N. C., et al., *J. Chem. Soc., Chem. Comm.*, 144-145, 1977; Krumdieck, C. L., et al., *Meth. Enzymol.*, 66, 523-529, 1980; Silks, V. F., Ph.D. Thesis, Univ of S. Carolina, 1-147, November 1989; all of which references are incorporated by reference.

STEP 3

Deprotection

The compounds of formula (VA or VB) are treated with a reagent which removes the $R_3$ and $R_4$ protecting groups to produce the compounds of formula (IA or IB). Suitable reagents are well known in the art of peptide synthesis (Greene, Th. W., "*Protective Groups in Organic Synthesis*", Wiley, New York, (1981), pages 152-187, which pages are incorporated by reference). Inorganic or organic bases and inorganic or organic acids are suitable. Examples of the bases include aqueous alkaline earth metal or alkali metal hydroxides, or tertiary or quarternary $C_1$-$C_4$ alkyl ammonium hydroxides; specifically magnesium, calcium, sodium and potassium hydroxides and trimethyl, triethyl, tetramethyl or tetraethyl ammonium hydroxides. Examples of the acids include trifluoroacetic acid, formic acid, aqueous HCl and HBr, and optionally in a water miscible solvent such as methanol, ethanol, isopropanol, acetonitrile, tetrahydrofuran, dioxane, DMF and the like.

Suitable tetrahydropteroylmono-L-glutamic acid derivatives for the preparation of their α-monoesters in STEP 1 include tetrahydrofolic acid, 5-methyl tetrahydrofolic acid, 5,10-methylene tetrahydrofolic acid, 5,10-methenyl tetrahydrofolic acid (with a suitable counterion selected from chloride, bromide, iodide, fluoride, formate, trifluoroacetate, acetate, sulfate, phosphate and the like), 5-formyl tetrahydrofolic acid, 5,10-diformyl tetrahydrofolic acid, 5-t-butoxy carbonyl-tetrahydrofolic acid and 5,10-di-t-butoxy carbonyl tetrahydrofolic acid. Folinic acid, however, is the preferred derivative of tetrahydropteroylmono-L-glutamic acid for the purpose of this invention. Most of the starting compounds are commercially available, also, see *Methods of Enzymology*, Vol. 6, pages 802-815, 1963, which is incorporated by reference. This reference teaches how to make several of these compounds.

The present invention extends to the monocationic salts and the α-monoesters of tetrahydropteroylmono-L-glutamic acid derivatives. The compounds of formula (III) are novel. Preferential salts being monoalkaline earth metals or alkali, monotertiary alkyl or quarternary alkyl ammonium ions, silver and lead.

The following examples serve to delineate the invention.

EXAMPLES

Example 1

Preparation of the α-2,6-Dichlorobenzyl Monoester of (6R,S) Folinic Acid 500 mg of (6R,S) folinic acid and 56 mg of $Na_2CO_3$ were added to 30 mL of dimethylsulfoxide (DMSO). 317 mg of α-2,6-dichlorobenzyl bromide is added and the mixture stirred at room temperature for 5 hours. The reaction mixture is then concentrated in vacuo and the resulting residue flash chromatographed [Still et al., *J. Org. Chem.* 43, 2923-2925 (1978)] over C8 (80:20 (v/v) 0.1M aqueous acetic acid/acetonitrile). The product containing fractions (50 mL) were combined and dried in vacuo to yield 325 mg of an approximately 8:1 ratio of the α/γ-2,6-dichlorobenzyl monoesters of folinic acid. The two isomers were resolved by high pressure liquid chromatography on a C18 column (70:30 (v/v) 0.1M aqueous acetic acid/acetonitrile) and dried in vacuo to yield 280 mg of the pure α-2,6-dichlorobenzyl monoester of folinic acid: mp >300° C.; IR (KBr) wavenumber 3345, 1730, 1620, 1325, 1188, 770; $^1$H 500 m Hz NMR (Me$_2$SO-d$_6$) delta 1.97 (cm,1H), 2.21(cm,2H), 2.33(cm,2H), 2.80(cm,1H), 3.07(cm,1H), 3.13(dd,J=4.1,12.6 Hz,1H), 3.41(dd,J=5.1,12.7,1H),4.21(q,J=7.5,1H),4.31(cm,1H)-,4.78(cm,1H), 5.26, 5.32(AB,J=12 Hz,2H), 6.31(bt,J=~5.0 Hz,1H), 6.57(d,J=8.7 Hz,2H), 6.69(bs,2H), 6.97(d,1H), 7.44(cm,J=7.3, 8.8 Hz,1H), 7.53(cm, J=7.9,2H), 7.60(vb,1H), 7.64(d,J=8.5 Hz,2H), 8.832(s,1H), 9.13(bs,1H), 11.3(bs,1H); MS(HRFAB) m/z found 632.1480(M+), calcd. for $C_{27}H_{27}Cl_2N_7O_7$ 632.1424 and 34 mg of the pure γ-2,6-dichlorobenzyl monoester of folinic acid: mp >300° C.; IR (Kbr) wavenumber 3345, 1722, 1620, 1325, 1188, 770; $^1$H 500 m Hz NMR (Me$_2$SO-d$_6$) delta 1.90(cm,1H), 2.20(cm,2H), 2.34(cm,2H), 2.86(cm,1H), 3.06(cm,1H), 3.12(dd,J=3.3,12.2 Hz,1H), 3.40(dd,J=4.4,12.2 Hz,1H), 4.2(q,J=7.1 Hz,1H), 4.80(cm,1H), 5.26(s,2H), 6.32(bt,J=~5.0 Hz,1H), 6.34(bs,2H), 6.60(d,J=8.5 Hz,2H), 6.97(d,1H), 7.43(cm,J=7.7,8.4 Hz,1H), 7.52(cm,J=7.9 Hz,2H), 7.62(d,J=8.4 Hz,2H), 7.8(bs,1H), 8.8(s,1H), 10.6(bs,1H), ~12 (folded); MS (HRFAB) m/z found 632.1366(M+), calcd. for $C_{27}H_{27}Cl_2N_7O_7$ 632.1424.

Example 2

Preparation of the α-2,6-Dichlorobenzyl, di-γ-L-glutamate diethyl triester of (6R,S) Folinic acid 260 mg of the (6R,S)-α-2,6-dichlorobenzyl monoester of folinic acid, 123 mg of L-glutamic acid diethyl ester hydrochloride, 106 mg of dicyclohexyl carbodiimide (DCC) and 69 mg of 1-hydroxybenzotriazole (HOBt) were added to 15 mL of dimethylformamide (DMF) containing 45 μL of 4-methylmorpholine. The reaction mixture is stirred for 16 hours at room temperature and concentrated in vacuo. The resulting residue is then chromatographed (Chromatotron) over silica (10:1 (v/v) methylene chloride/methanol) and dried to yield 262 mg of the α-2,6-dichlorobenzyl, di-γ-glutamate diethyl triester of folinic acid: mp >300° C.; IR (Kbr) wavenumber 3325, 1730, 1625, 1335, 1185, 770; $^1$H 500 m Hz NMR delta 1.154, 1.157(two (t), J=7.1 Hz,6H), 1.79(cm,1H), 1.94(cm,2H), 2.05(cm,1H), 2.26(cm,2H), 2.33(cm,2H), 2.87(td,J=5.1,13.5 Hz,1H), 3.07(ddd,J=6.6,8.1,13.5 Hz,1H), 3.13(dd,J=4.1,12.5 H,1H), 3.41(dd,J=5.0,12.2 Hz,1H), 4.03, 4.04 (two (q),J=7.2 Hz,4H), 4.21(ddd,J=5.4,7.5,8.8 Hz,1H), 4.4(cm, v=25 Hz,1H), 4.8 (cm,1H), 5.28,5.33(AB,J=12.0 Hz,2H), 6.20(bs,2H), 6.36(t,J=5.7 Hz,1H), 6.61 (d,J=8.7 Hz,2H), 6.98(d,J=4.6 Hz,1H), 7.45(cm,J=7.3,8.8 Hz,1H), 7.53(cm,J=8.0 Hz,2H), 7.66(d,J=8.7 Hz,2H), 8.23(d,J=7.4 Hz,1H), 8.45(s,1H), 10.22(s,1H); MS (FAB) relative intensity m/z 817(MH$^+$,8).

Example 3

Preparation of the Triammonium Salt of (6R,S) Folinic di-γ-L-glutamic acid 5 mL of 0.1N NaOH is added to 10 mL of a 50:50 (v/v) p-dioxane/H$_2$O solution which contains 262 mg of the α-2,6-dichlorobenzyl, di-γ-L-glutamate diethyl triester. The reaction mixture is stirred for 6 hours at room temperature, cooled to 4° C. and the pH adjusted to 7.0 with acetic acid. The solution is then chromatographed over cellulose (60:40 (v/v) 0.5M NH$_4$HCO$_3$./EtOH) and dried in vacuo to yield 184 mg of the triammonium salt of (6R,S) folinic di-γ-glutamic acid: MS(FAB) relative intensity m/z 691(MNa$_4$$^+$,23), 669(MNa$_3$$^+$,22). Examples 1-3 are illustrated in Scheme 1. Scheme 2 shows the method in general.

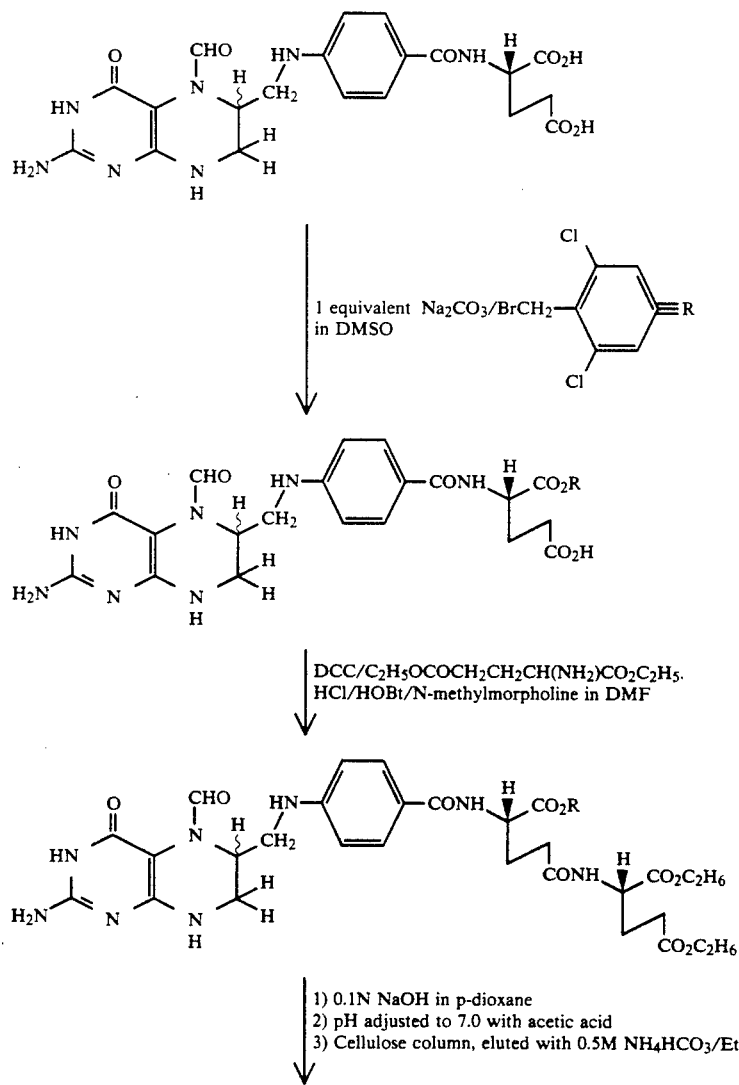

Scheme 1

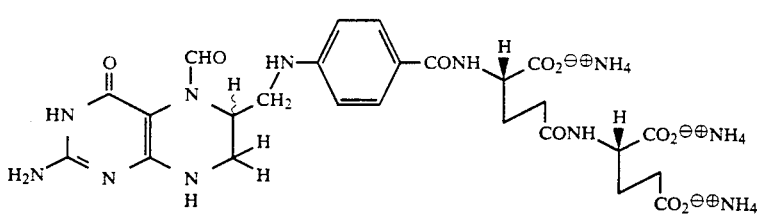

Scheme 2

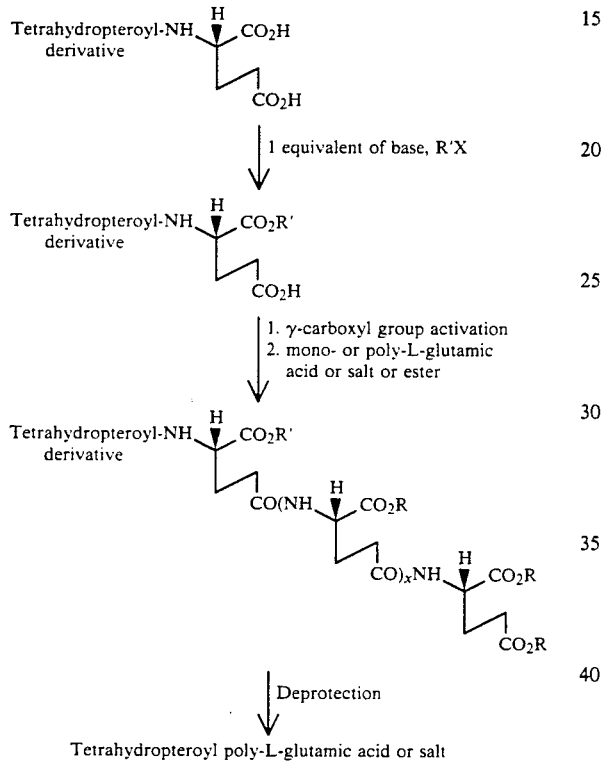

What is claimed is:

1. A method of synthesizing tetrahydtropteroylpoly-L-glutamic acid compounds of the formula (IA) or (IB)

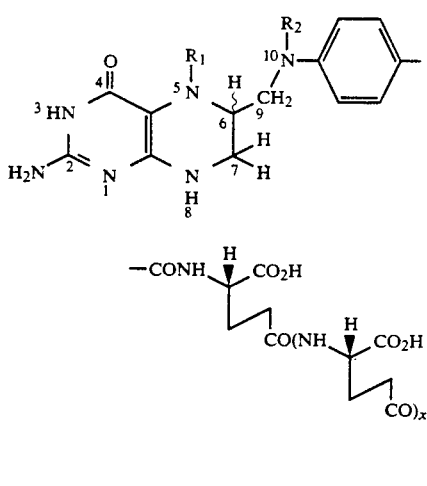 (IA)

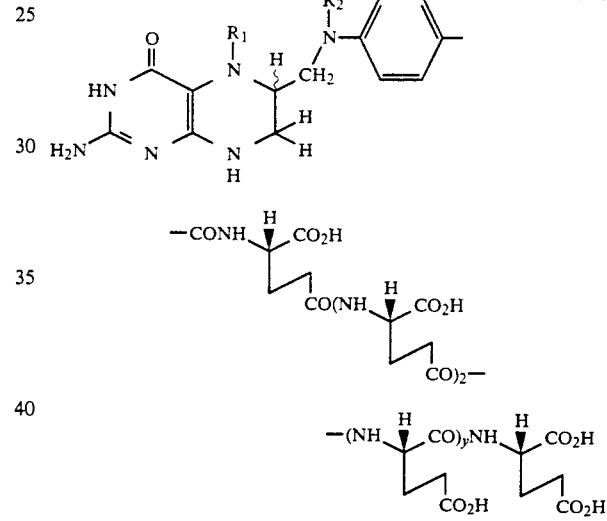 (IB)

wherein x is 0 to 14; y is 1 to 15; $R_1$ and $R_2$ are independently H, $C_1$–$C_6$ alkyl, $C_1$–$C_6$ alkylcarbonyl, $C_1$–$C_6$ alkoxycarbonyl, $C_6$–$C_{10}$ arylcarbonyl, $C_6$–$C_{10}$ aryloxycarbonyl or —CHO; or $R_1$ and $R_2$ together form a one carbon bridge between the nitrogen atoms at the 5 and 10 positions; and wherein the chiral carbon atom at position 6 is in the R, S or mixtures of R and S configurations; said method comprising:

a) esterifying a compound of formula (II)

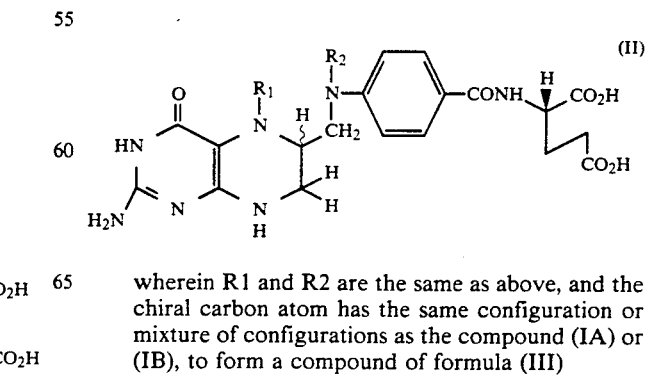 (II)

wherein R1 and R2 are the same as above, and the chiral carbon atom has the same configuration or mixture of configurations as the compound (IA) or (IB), to form a compound of formula (III)

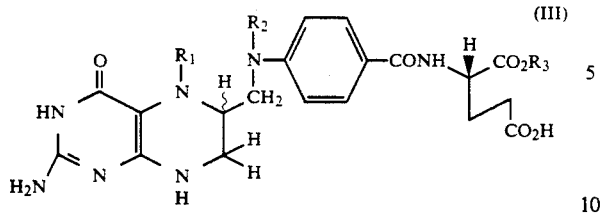
(III)

wherein $R_1$ and $R_2$ are the same as above, and $R_3$ is $C_1$-$C_8$ alkyl, substituted $C_1$-$C_8$ alkyl, $C_5$-$C_6$ cycloalkyl, substituted $C_5$-$C_6$ cycloalkyl, $C_6$-$C_{10}$ aryl, substituted $C_6$-$C_{10}$ aryl, $C_6$-$C_{10}$ aryl $C_1$-$C_8$ alkyl, substituted $C_6$-$C_{10}$ aryl $C_1$-$C_8$ alkyl, diphenylmethyl, substituted diphenylmethyl and tri $C_1$-$C_4$ alkylsilyl, wherein the substituents in said substituted alkyl, cycloalkyl, aryl, arylalkyl and diphenylmethyl are up to 3 in number and are chosen from the group consisting of methyl, ethyl, $C_1$-$C_3$ alkoxy, $C_1$-$C_3$ thioalkoxy and halogen;

b) coupling a compound of formula (III) with a compound of formula (IVA) or (IVB)

(IVA)

(IVB)

wherein x is 0 to 14; y is 1 to 15; and $R_4$ is defined the same as $R_3$, to form a compound of formula (VA) or formula (VB)

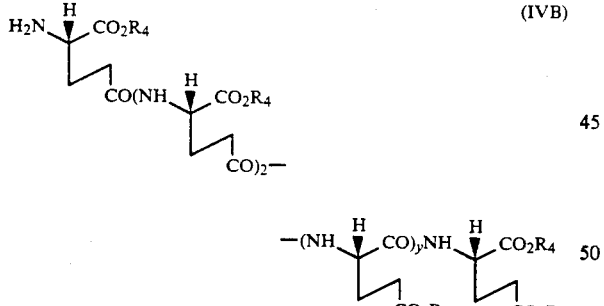
(VA)

(VB)

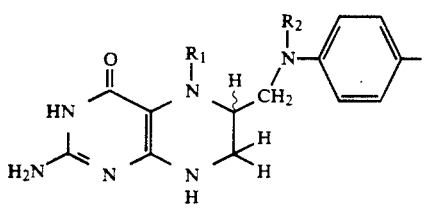

c) deprotecting the compound of formula (VA) or (VB) by treatment with a reagent which removes the $R_3$ and $R_4$ moieties to produce the compound of formula (IA) or (IB).

2. The method of claim 1, wherein $R_3$ is $C_1$-$C_6$ alkyl, substituted $C_1$-$C_6$ alkyl, $C_5$-$C_6$ cycloalkyl, phenyl, substituted phenyl, benzyl, substituted benzyl, diphenylmethyl or triethylsilyl.

3. The method of claim 2, wherein said $R_3$ group is methyl, ethyl, propyl, butyl, sec-butyl, t-butyl, pentyl, hexyl, cyclopentyl, cyclohexyl, methoxymenthyl, ethoxymethyl, methylthiomethyl, 2,2,2-trichloroethyl, 2-bromoethyl, phenyl, benzyl, 2-chlorobenzyl, 2,6-dichlorobenzyl, diphenylmethyl or triethylsilyl.

4. The method of claim 3, wherein the compound of formula (II) is tetrahydrofolic acid, 5-methyl-tetrahydrofolic acid, 5,10-methylene-tetrahydrofolicacid,5,10-methenyl-tetrahydrofolicacid, 5-formyl-tetrahydrofolic acid, 5,10-diformyl-tetrahydrofolic acid, 5-t-butoxycarbonyl-tetrahydrofolic acid or 5,10-di-t-butoxycarbonyl-tetrahydrofolic acid.

5. The method of claim 1, wherein said esterifying step a) comprises reacting said compound of formula (II) with a compound of formula $R_3$-X, wherein $R_3$ is as defined in claim 1 and X is halogen.

6. The method of claim 5, wherein X is bromine.

7. The method of claim 1, wherein said coupling of step b) comprises activation of the γ-carboxyl group of the compound of formula (III) with DCC, EEDQ, 1',1'-carbonyldiimidazole or diphenylchlorophosphate.

8. The method of claim 1, wherein said reagent of step c) is an organic base, inorganic base, organic acid or inorganic acid.

9. The method of claim 8, wherein said organic base or inorganic base is an alkaline earth metal hydroxide, alkali metal hydroxide, a tertiary $C_1$-$C_4$ alkyl ammonium hydroxide or a quarternary $C_1$-$C_4$ alkyl ammonium hydroxide.

10. The method of claim 8, wherein said organic acid or inorganic acid is trifluoroacetic acid, formic acid, HCl or HBr.

* * * * *